US 9,681,795 B2

(12) United States Patent
Yasunaga

(10) Patent No.: US 9,681,795 B2
(45) Date of Patent: Jun. 20, 2017

(54) ENDOSCOPE HOLDING APPARATUS

(71) Applicant: OLYMPUS CORPORATION, Tokyo (JP)

(72) Inventor: Koji Yasunaga, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/358,655

(22) Filed: Nov. 22, 2016

(65) Prior Publication Data

US 2017/0071454 A1 Mar. 16, 2017

Related U.S. Application Data

(63) Continuation of application No. PCT/JP2015/076003, filed on Sep. 14, 2015.

(30) Foreign Application Priority Data

Mar. 27, 2015 (JP) ................. 2015-066724

(51) Int. Cl.
*A61B 1/00* (2006.01)
*G02B 23/24* (2006.01)

(52) U.S. Cl.
CPC ............ *A61B 1/00149* (2013.01); *A61B 1/00* (2013.01); *G02B 23/24* (2013.01)

(58) Field of Classification Search
CPC ....... A61B 1/00; A61B 1/00149; A61B 90/25; A61B 90/50; A61B 2090/504; A61B 2090/506; G02B 23/24
See application file for complete search history.

(56) References Cited

U.S. PATENT DOCUMENTS 5,825,536 A    10/1998   Yasunaga et al.

FOREIGN PATENT DOCUMENTS

| EP | 0 700 665 A1 | 3/1996 |
|---|---|---|
| JP | H07-227398 A | 8/1995 |
| JP | H08-131457 A | 5/1996 |
| JP | H08-266555 A | 10/1996 |
| JP | 2001-258903 A | 9/2001 |
| JP | 2004-105726 A | 4/2004 |
| JP | 2004-209096 A | 7/2004 |
| JP | 2004-358239 A | 12/2004 |
| JP | 2009-297236 A | 12/2009 |
| JP | 5265818 B2 | 8/2013 |

OTHER PUBLICATIONS

International Search Report dated Dec. 15, 2015 issued in PCT/JP2015/076003.

*Primary Examiner* — Timothy J Neal
(74) *Attorney, Agent, or Firm* — Scully, Scott, Murphy & Presser, PC

(57) ABSTRACT

An endoscope holding apparatus includes: a base section; a support column; a first link and a second link that rotate around a first linking portion; a third link that rotates around a second linking portion; a fourth link capable of holding an endoscope; a fifth link including a first counter weight; a second counterweight linked to the second linking portion; a sixth link including one arm linked to the fifth link; and a seventh link including a first end configured to rotate around a fifth linking portion and a second end configured to rotate around a sixth linking portion, wherein the first, fifth, sixth, and third linking portions form a parallelogram.

2 Claims, 6 Drawing Sheets

ENDOSCOPE HOLDING APPARATUS

CROSS REFERENCE TO RELATED APPLICATION

This application is a continuation application of PCT/JP2015/076003 filed on Sep. 14, 2015 and claims benefit of Japanese Application No. 2015-066724 filed in Japan on Mar. 27, 2015, the entire contents of which are incorporated herein by this reference.

BACKGROUND OF THE INVENTION

1. Field of the Invention

The present invention relates to an endoscope holding apparatus which holds a medical instrument such as an endoscope in place of a surgeon and which is capable of maintaining the held medical instrument at an arbitrary position.

2. Description of Related Art

In recent years, surgeries using an endoscope, for example, laparoscopic surgeries have been performed. A surgery using an endoscope has an advantage of being capable of reducing a burden on a patient, since the incision range is small compared with that in normal surgeries. A rigid endoscope for observing an inside of a body cavity is widely used for the above-described kind of surgery under the observation of an endoscope. Such a rigid endoscope is used by being inserted into an abdominal cavity through a guide member such as a trocar punctured into an abdominal wall. During the surgery, the endoscope is generally held by a surgeon or a supporting staff (assistant) called scopist. The surgeon or the scopist observes a desired site in a body cavity by performing advancing/retracting operation, turning operation, tilting operation and the like of the endoscope during the surgery.

In addition, in recent years, an endoscope holding apparatus that mechanically holds an endoscope or a treatment instrument (hereinafter, referred to as endoscope or the like) to be used in a laparoscopic surgery or the like in place of a surgeon or a scopist has been proposed. With the use of such an endoscope holding apparatus, efficient surgeries have been performed by reducing a load on the surgeon or scopist and reducing the number of the staff involved in the surgeries.

As a conventional configuration of the endoscope holding apparatus, for example, a holding arm apparatus has been proposed that includes a base section configured to be movable in a space available for a surgery (clinical room such as a surgery room or the like) and a holding arm attached to a support column portion placed vertically at the base section. The holding arm apparatus is provided with a holding instrument configured to hold the endoscope or the like.

The endoscope holding apparatus as described above is configured to be capable of attaching the endoscope or the like to the holding instrument and moving the endoscope or the like in up/down direction and horizontal direction with a light load in the state where the endoscope is held by the holding instrument, and capable of maintaining the endoscope or the like at a desired arbitrary position.

The endoscope holding apparatus thus configured provides effects of enabling the field of view of the endoscope to be stably ensured, enabling the field of view to be minutely changed, enabling the endoscope or the like to be moved only with a small amount of force as a surgeon or the like intends at the time of changing the field of view, and enabling a desired arbitrary position of the endoscope or the like to be surely maintained.

In the conventional endoscope holding apparatus, as an ingenuity for freely moving the held endoscope or the like with a light load and also surely maintaining the desired arbitrary position of the held endoscope or the like, the endoscope holding arm is configured to hold the endoscope or the like at one end and includes a counterweight at a predetermined site on the other end which is opposite to the one end across a support shaft.

Such a configuration enables the attached endoscope or the like to be held in good balance and to be moved rapidly with a light load, and also enables the endoscope or the like to be stopped on the spot when the load is not applied, to thereby be capable of surely maintaining the position of the endoscope or the like.

Various types of such endoscope holding apparatuses of what is called a counterweight balance type thus configured have been proposed by Japanese Patent No. 5265818, Japanese Patent Application Laid-Open Publication No. 7-227398, Japanese Patent Application Laid-Open Publication No. 2001-258903, Japanese Patent Application Laid-Open Publication No. 2004-209096, Japanese Patent Application Laid-Open Publication No. 2009-297236, etc., for example, and put into practical use.

SUMMARY OF THE INVENTION

An endoscope holding apparatus according to one aspect of the present invention includes: a base section; a support column connected to the base section; a first link including a short arm portion, a long arm portion, and a first protruding portion that are extended from a base portion, the base portion being rotatably linked to the support column at a first linking portion; a second link rotatably linked to the support column and the first link at the first linking portion; a third link rotatably linked to the second link at a second linking portion provided at the second link; a fourth link rotatably linked to the first link and the third link, and configured to maintain the first link and the third link in parallel with each other, the fourth link being maintained in parallel with the second link and configured to be capable of holding an endoscope at an end portion the fourth link; a fifth link including a first end and a second end, the first end being rotatably linked to an end portion of the short arm portion of the first link, the fifth link including a first counterweight which is hanged in a vertical direction at a middle portion between the first end and the second end; a second counterweight rotatably linked to the second linking portion and hanged in the vertical direction; a sixth link including one arm portion and a second protruding portion that are extended from a base portion, the base portion being rotatably linked to the support column at a third linking portion, the one arm portion being rotatably linked to the second end of the fifth link at a fourth linking portion, the one arm portion being maintained in parallel with the first link; and a seventh link including a first end and a second end, the first end being rotatably linked at a fifth linking portion of the first protruding portion, the second end being rotatably linked at a sixth linking portion of the second protruding portion, wherein the first linking portion, the fifth linking portion, the sixth linking portion, and the third linking portion are disposed at positions that form a parallelogram.

The present invention is capable of providing an endoscope holding apparatus configured to hold an endoscope or the like to be used in a surgery in place of a surgeon and enable an effective use of an installation site of the apparatus by narrowing a displacement region of a side where a counterweight is placed while ensuring a necessary moving region of the held endoscope or the like, to thereby enable smooth operation to be ensured.

DETAILED DESCRIPTION OF THE PREFERRED EMBODIMENTS

Figure 1:
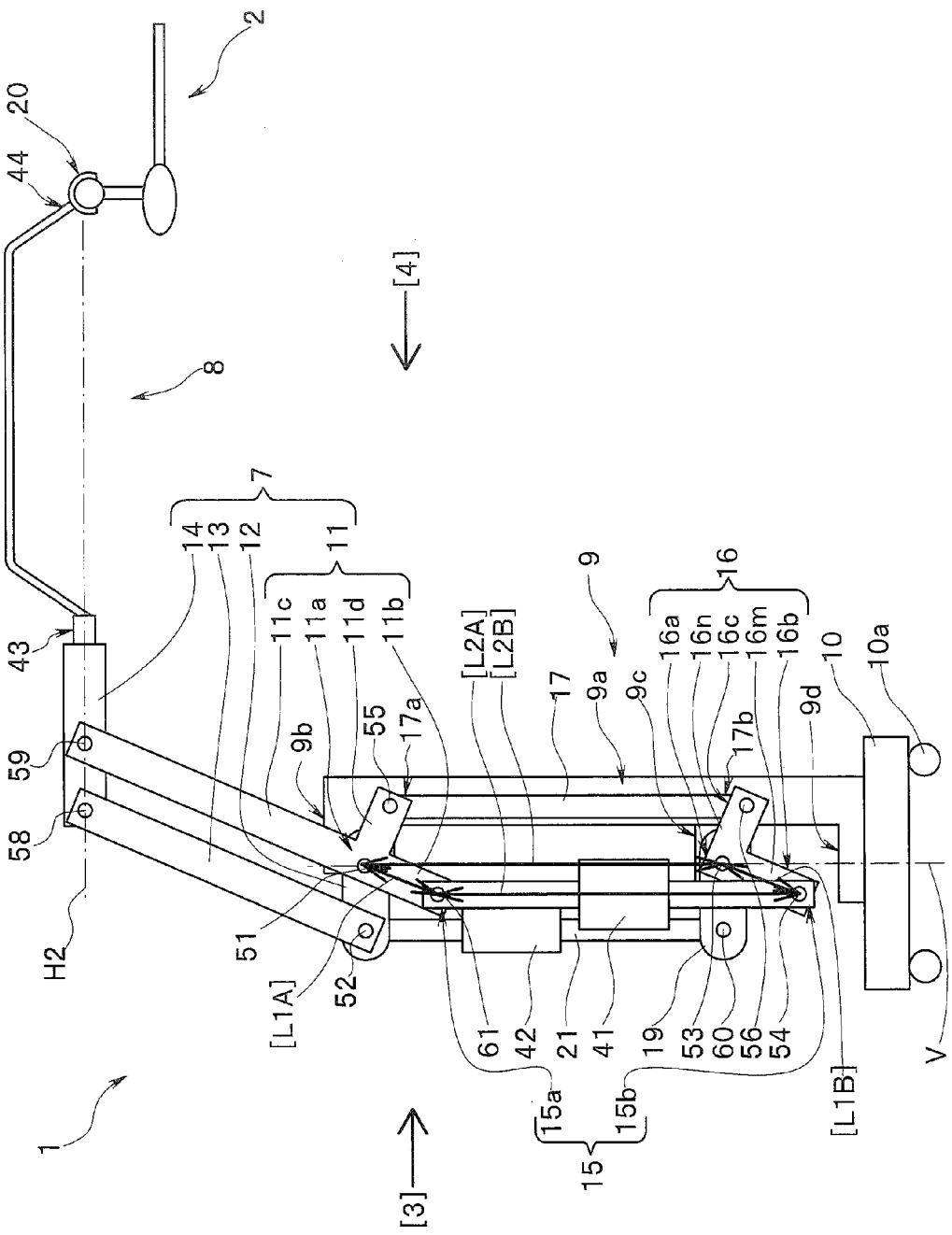
FIG. 1 is a schematic configuration diagram of an endoscope holding apparatus according to a first embodiment of the present invention.

Hereinafter, the present invention will be described with reference to embodiments shown in the drawings. Each of the drawings used in the description below is a schematic diagram, and there is a case where a different scale size is used for each of the constituent elements in order to allow each of the constituent elements to be illustrated in a recognizable size in each of the drawings. Therefore, the present invention is not limited only to the number or shapes of the constituent elements, a ratio of the sizes of the constituent elements, and a relative positional relationship among the constituent elements shown in these drawings.

First Embodiment

Figure 2:
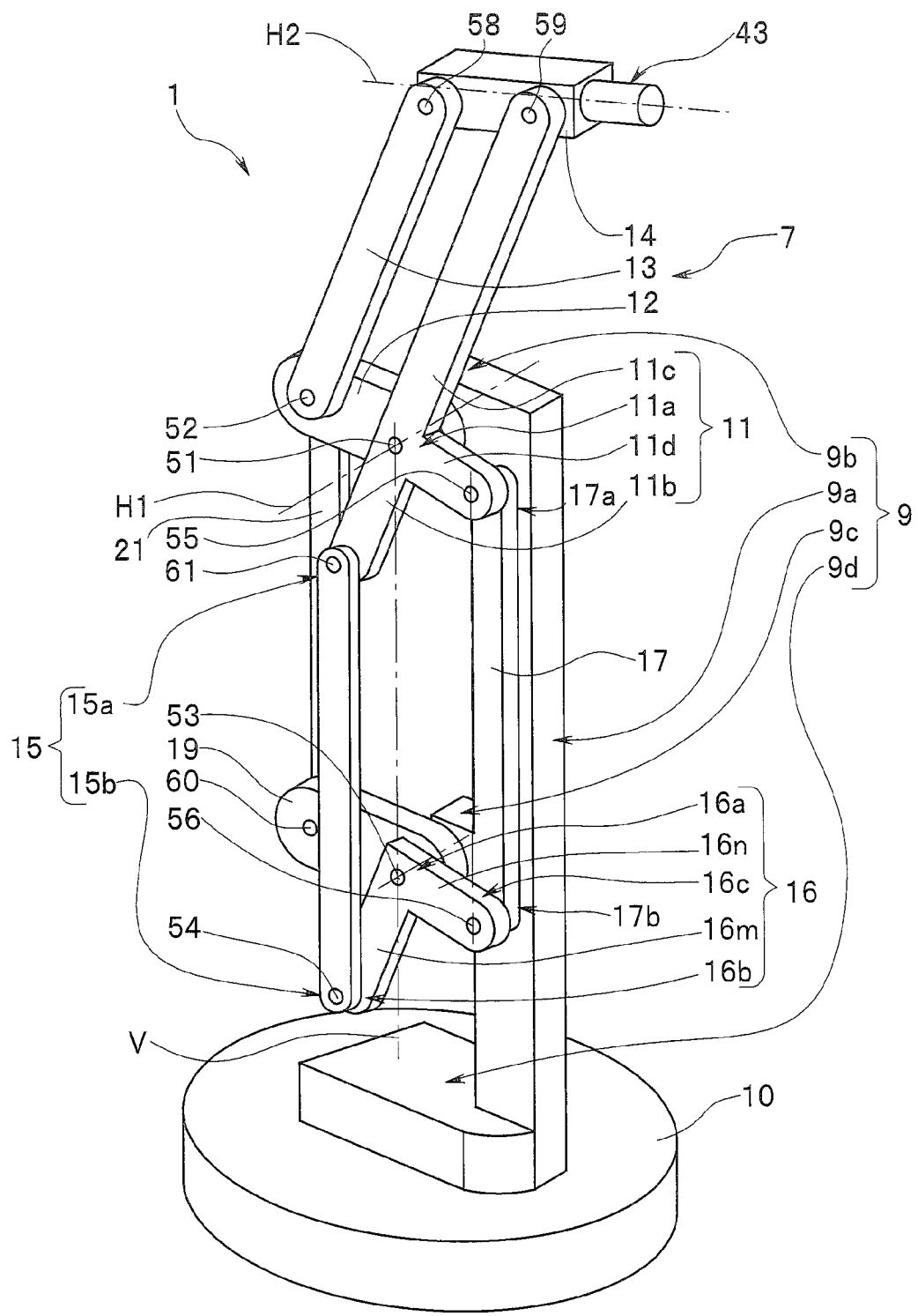
FIG. 2 is a perspective view showing a main configuration part of the endoscope holding apparatus in FIG. 1.
Figure 3:
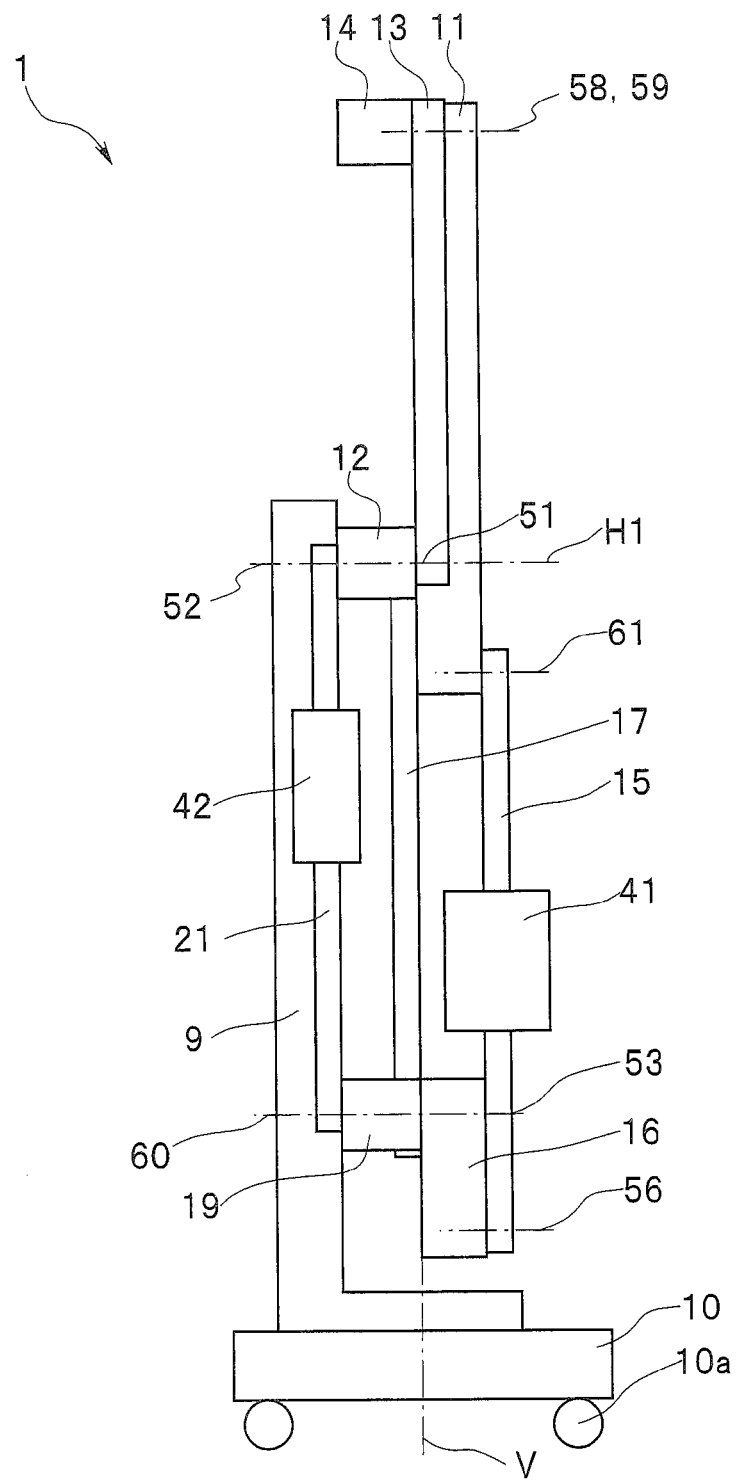
FIG. 3 is a main configuration diagram of the endoscope holding apparatus viewed from the direction of the arrow sign [3] in FIG. 1.
Figure 4:
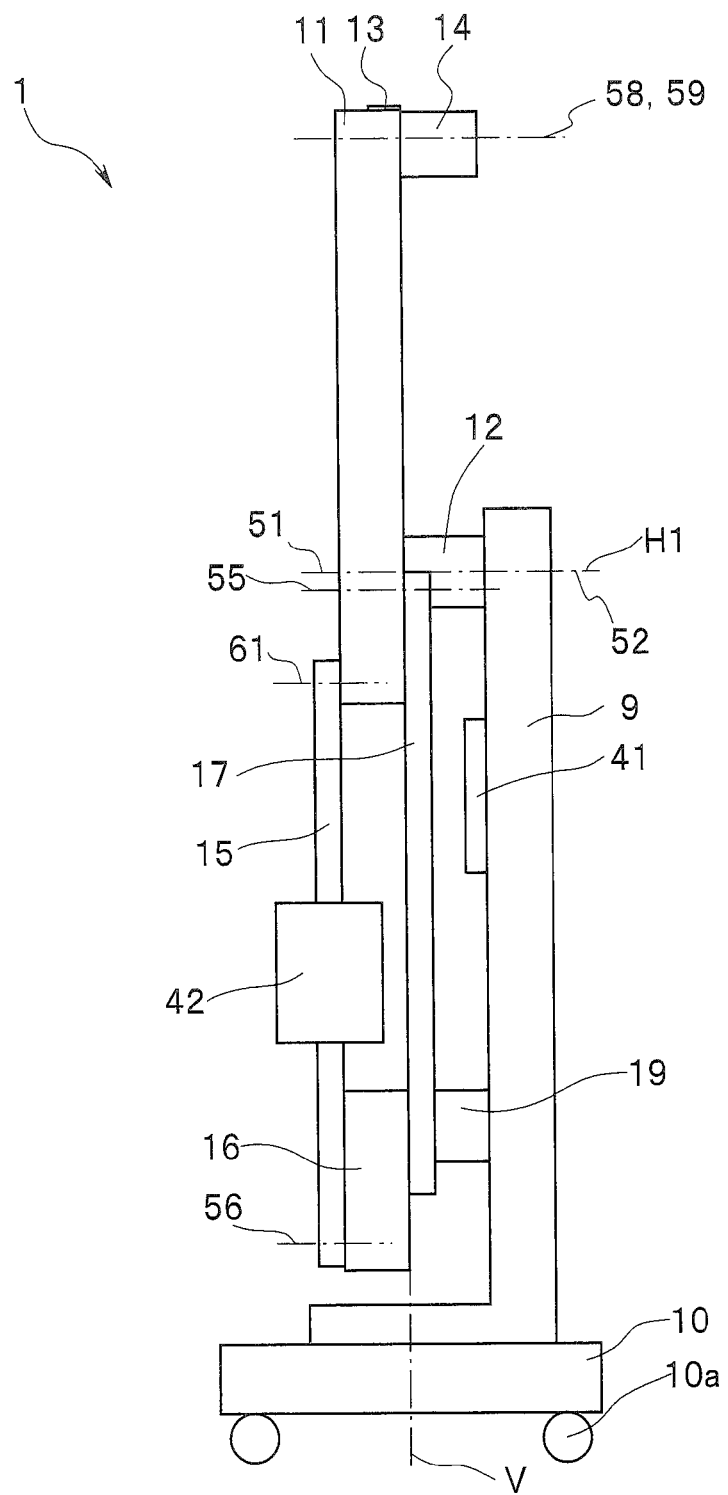
FIG. 4 is a main configuration diagram of the endoscope holding apparatus viewed from the direction of the arrow sign [4] in FIG. 1.

FIGS. 1 to 4 illustrate an endoscope holding apparatus according to the first embodiment of the present invention. Among the drawings, FIG. 1 is a schematic configuration diagram showing the state where a medical instrument such as an endoscope is held by an endoscope holding apparatus according to the present embodiment. FIG. 2 is a perspective view showing a main configuration part of the endoscope holding apparatus according to the present embodiment. FIG. 3 is a main configuration diagram of the endoscope holding apparatus viewed from the direction of the arrow sign [3] in FIG. 1. FIG. 4 is a main configuration diagram of the endoscope holding apparatus viewed from the direction of the arrow sign [4] in FIG. 1. Note that, in FIGS. 2 to 4, illustrations of a support arm portion that holds an endoscope or the like and the medical instrument such as the endoscope held by the support arm are omitted, and only the main configuration part of the endoscope holding apparatus according to the present embodiment is shown.

The endoscope holding apparatus 1 according to the present embodiment is arranged in a clinical room such as a surgery room, an examination room, or a treatment room, for example, and configured to hold a medical instrument such as a microscope, an endoscope, or a treatment instrument that is used during a surgery. The endoscope holding apparatus 1 is configured to be capable of freely moving the position of the medical instrument in a three-dimensional space, regardless of surrounding environments. With such a configuration, the endoscope holding apparatus 1 is capable of causing the held medical instrument to sufficiently exert the function thereof, reducing the burden on professionals who are involved in the surgery, i.e., a surgeon (user) such as doctor, a scopist, and the like, to thereby reduce the feeling of fatigue of the professionals, and reducing the number of the staffs involved in the surgery. Therefore, the endoscope holding apparatus 1 is a medical apparatus for carrying out an efficient surgery.

As shown in FIG. 1, the endoscope holding apparatus 1 is configured such that a parallelogram link mechanism 7 is supported at a base 10 as a base section placed on the floor of the clinical room, through a support column 9. The parallelogram link mechanism 7 has one end to which a support arm 8 is linked. At the distal end side of the support arm 8, a holding portion 20 is linked. An endoscope 2 which is a kind of medical instrument is attached to the holding portion 20. With such a configuration, the endoscope 2 is freely movable together with the holding portion 20 and the support arm 8 in the up/down direction and the horizontal direction and can also be stably held at a desired arbitrary position by the support column 9 and the parallelogram link mechanism 7, while being held by the holding portion 20. Note that the support arm 8, the holding portion 20, and the endoscope 2 are illustrated only in FIG. 1, and illustrations of the part configured by these elements are omitted in FIG. 2 and subsequent drawings.

The base 10 is a support body including, on the bottom surface side thereof, a plurality of casters 10a, and having an entire shape formed in a block shape or a plate shape. With such a configuration, the base 10 is movable on the floor in the space available for the surgery (i.e., surgery room or the like), for example. Note that the base 10 may be further provided with rotation preventing means for preventing the rotation of the casters 10a, or braking means or fixing means for preventing the base 10 from moving on the floor unintentionally (not shown). The configuration of the rotation prevention means, braking means, or the fixing means may be an existing one, and detailed description thereof will be omitted.

On the upper surface of the base 10, the support column 9 is rotatably connected and vertically provided, with the vertical axis V as a rotation center. The support column 9 is formed by a pole portion 9a that extends in the vertical direction, a first arm portion 9b that extends in the horizontal direction from the upper end portion of the pole portion 9a, a second arm portion 9c that extends in the horizontal direction from about the middle portion of the pole portion 9a, and a proximal end portion 9d that extends in the horizontal direction from the proximal end of the pole portion 9a.

The parallelogram link mechanism 7 is a configuration unit pivotally supported so as to be rotatable with a horizontal axis H1 (see FIG. 2) as a rotation center, the horizontal axis passing through a first linking portion 51, which is provided in the vicinity of the distal end of the first arm portion 9b of the support column 9, in the horizontal direction.

The parallelogram link mechanism 7 is configured by four link members, that is, a first link 11, a second link 12, a third link 13, and a fourth link 14. Among the link members, the first link 11 and the third link 13 are arranged in parallel with each other. In addition, the second link 12 and the fourth link 14 are arranged in parallel with each other and the links 12 and 14 are arranged in a same one surface orthogonal to the horizontal axis H1.

The first link 11 is formed by including a short arm portion 11b as one arm portion, a long arm portion 11c as the other arm portion, and a first protruding portion 11d, which are each extended from a base portion 11a. The short arm portion 11b, the long arm portion 11c, and the first protruding portion 11d are the parts extending radially at an interval of 90 degrees in the circumferential direction with the base portion 11a as a center. In addition, the base portion 11a of the first link 11 is rotatably linked to the support column 9 at the first linking portion 51. That is, the first link 11 is rotatably linked at the first linking portion 51 of the first arm portion 9b of the support column 9, with the base portion 11a as the rotation center. In other words, the first link 11 is pivotally supported so as to be rotatable, with the horizontal axis H1 (see FIG. 2) as the rotation center, at the first linking portion 51 located in the vicinity of the distal end of the first arm portion 9b of the support column 9. Therefore, the parallelogram link mechanism 7 is rotatable, with the horizontal axis H1 as the rotation center, in the plane vertical to the horizontal axis H1.

An eleventh linking portion 61 is provided in the vicinity of the distal end of the short arm portion 11b of the first link 11, and a first end 15a of a fifth link 15 is rotatably linked at the eleventh linking portion 61. The fifth link 15 includes, at a middle portion thereof, a first counterweight 41, and hanged in the vertical direction. Since the fifth link 15 that holds the first counterweight 41 is thus disposed so as to be hanged in the vertical direction, it is enabled to suppress the protruding amount of the counterweight.

In addition, one arm portion 16m of a sixth link 16 to be described later is rotatably linked to a second end 15b of the fifth link 15. Though detailed description will be made later, the other end (the second end 15b on the lower end side) of the fifth link 15 hanged in the vertical direction is linked with the one arm portion 16m of the sixth link 16 as a parallel link which is paired up with the short arm portion 11b of the first link 11, which prevents the counterweight in the hanged state from swinging. As a result, stable operation can be ensured.

Note that illustration of the first counterweight 41 is omitted in FIG. 2. The fifth link 15 itself shown in FIG. 2 may be configured to function as the first counterweight by configuring the fifth link 15 itself by using a material having a weight. The counterweight is thus formed in an elongated shape, for example, to thereby enable the protruding region of the counterweight to be further reduced.

In the vicinity of the distal end of the long arm portion 11c of the first link 11, a ninth linking portion 59 is provided, and the first link is rotatably linked to the middle portion of the fourth link 14 at the ninth linking portion 59.

In the vicinity of the distal end of the first protruding portion 11d of the first link 11, a fifth linking portion 55 is provided, and a first end 17a of a seventh link 17 is rotatably linked to the first link 11 at the fifth linking portion 55. In addition, at the second end 17b of the seventh link 17, a sixth linking portion 56 is provided, and a second protruding portion 16n of a sixth link 16 to be described later is rotatably linked to the seventh link 17 at the sixth linking portion 56.

The second link 12 has one end rotatably linked to the support column 9 and the first link 11 at the first linking portion 51. In addition, the second link 12 includes at the other end thereof a second linking portion 52, and one end of the third link 13 and one end of a second weight holding link 21 to be described later are rotatably linked to the second link 12 at the second linking portion 52.

The third link 13 has one end rotatably linked to the second link 12 (and the second weight holding link 21) at the second linking portion 52 of the second link 12. In addition, the third link 13 includes at the other end thereof an eighth linking portion 58, and the one end of the fourth link 14 is rotatably linked to the third link 13 at the eighth linking portion 58.

The fourth link 14 has the one end rotatably linked to the third link 13 at the eighth linking portion 58. Furthermore, the fourth link 14 includes, at the middle portion thereof, the ninth linking portion 59, and the distal end of the long arm portion 11c of the first link 11 is rotatably linked to the fourth link 14 at the ninth linking portion 59. The support 8 (shown only in FIG. 1) is linked to the other end of the fourth link 14 at a proximal end linking portion 43, and the holding portion 20 is linked to the distal end side of the support arm 8 at a distal end linking portion 44. The holding portion 20 thus holds the endoscope 2. The fourth link 14 is maintained in parallel with the second link 12. In addition, the first link 11 is maintained in parallel with the third link 13. The parallelogram link mechanism 7 is thus configured.

In the parallelogram link mechanism 7, the respective rotational shafts of the first linking portion 51, the second linking portion 52, the eighth linking portion 58, and the ninth linking portion 58 are arranged so as to be in parallel with the horizontal axis H1. The first linking portion 51 rotatably links the first link 11 and the second link 12. The second linking portion 52 rotatably links the second link 12 and the second weight holding link 21. The eighth linking portion 58 rotatably links the third link 13 and the fourth link 14. The ninth linking portion 58 rotatably links the first link 11 and the fourth link 14.

On one hand, as described above, the first end 15a of the fifth link 15 that holds at the middle portion thereof the first counterweight 41 is rotatably linked to the eleventh linking portion 61 of the short arm portion 11b of the first link 11. In the present embodiment, the first counterweight 41 is arranged so as to be held by the short arm portion 11b and the fifth link 15 that move along a surface orthogonal to a surface including the vertical axis V and the horizontal axis H1. The first counterweight 41 can be changed or the arranging position of the counterweight can be changed depending on the weight of the endoscope 2, for example.

On the other hand, the one end of the third link 13 and the one end of the second weight holding link 21 are rotatably linked to the second linking portion 52 of the second link 12. The second weight holding link 21 holds at the middle portion thereof a second counterweight 42 and is hanged in the vertical direction. Since the second weight holding link 21 that holds the second counterweight 42 is thus disposed so as to be hanged in the vertical direction, it is enabled to suppress the protruding amount of the counterweight.

In addition, the second weight holding link 21 has the other end to which a tenth linking portion 60 at the distal end of the ninth link 19 is rotatably linked Since the other end (lower end side) of the second weight holding link 21 hanged in the vertical direction is linked with the ninth link 19 as a parallel link which is paired up with the second link 12, it is enabled to prevent the counterweight in the hanged state from swinging. As a result, stable operation can be ensured.

Note that illustration of the second counterweight 42 is omitted in FIG. 2. The second weight holding link 21 itself shown in FIG. 2 may be configured to function as the second counterweight by configuring the second weight holding link 21 itself by using a material having a weight. The counterweight is thus formed in an elongated shape, for example, to thereby enable the protruding region of the counterweight to be further reduced.

The proximal end of the ninth link 19 is rotatably linked to the second arm portion 9c of the support column 9. That is, the second arm portion 9c of the support column 9 is provided with a third linking portion 53, and the proximal end of the ninth link 19 is rotatably linked to the second arm portion 9c at the third linking portion 53. In addition, a base portion 16a of the sixth link 16 is rotatably linked at the third linking portion 53.

The sixth link 16 has the one arm portion 16m and the second protruding portion 16n, which are each extended from the base portion 16a. The one arm portion 16m and the second protruding portion 16n are the parts extending radially at an interval of 90 degrees in the circumferential direction, with the base portion 16a as a center. The sixth link 16 is thus formed in substantially an L-shape.

The base portion 16a of the sixth link 16 is rotatably linked to the support column 9 at the third linking portion 53. Also the proximal end of the ninth link 19 is rotatably linked at the third linking portion 53.

The fourth linking portion 54 is provided at the distal end vicinity 16b of the one arm portion 16m of the sixth link 16, and the second end 15b of the fifth link 15 is rotatably linked to the sixth link 16 at the fourth linking portion 54, as described above. In addition, the distal end vicinity 16c of the second protruding portion 16n of the sixth link 16 is rotatably linked to the seventh link 17 at the sixth linking portion 56 of the second end 17b of the seventh link 17. Such a configuration allows the one arm portion 16m of the sixth link 16 to be maintained in parallel with the first link 11. Further, the second protruding portion 16n of the sixth link 16 is maintained in parallel with the first protruding portion 11d of the first link 11. Furthermore, the seventh link 17 and the fifth link 15 are maintained in parallel with each other.

In the present embodiment, a line connecting the first linking portion 51 and the third linking portion 53 is set so as to substantially coincide with the vertical axis V as the rotation center of the support column 9. Note that at least the first linking portion 51 has only to be arranged on the vertical axis V.

A parallelogram is formed by the line connecting the first linking portion 51 and the third linking portion 53, the second weight holding link 21, the second link 12, and the ninth link 19. In other words, the first linking portion 51, the third linking portion 53, the tenth linking portion 60, and the second linking portion 52 are disposed at the positions that form the parallelogram, to thereby configure the (first) parallelogram link mechanism. The (first) parallelogram link mechanism functions as counterweight inclination restricting means that restricts the inclination of the second counterweight 42 to constantly maintain the state where the counterweight is hanged in the vertical direction.

Similarly, a parallelogram is formed by the line connecting the first linking portion 51 and the third linking portion 53, the fifth link 15, the short arm portion 11b of the first link 11, and the one arm portion 16m of the sixth link 16. In other words, the first linking portion 51, the third linking portion 53, the fourth linking portion 54, and the eleventh linking portion 61 are disposed at the positions that form the parallelogram, to thereby configure the (second) parallelogram link mechanism. The (second) parallelogram link mechanism functions as counterweight inclination restricting means that restricts the inclination of the first counterweight 41 to constantly maintain the state where the first counterweight 41 is hanged in the vertical direction.

Furthermore, a parallelogram is formed by the line connecting the first linking portion 51 and the third linking portion 53, the seventh link 17, the second protruding portion 16n of the sixth link 16, and the first protruding portion 11d of the first link 11. In other words, the first linking portion 51, the third linking portion 53, the sixth linking portion 56, and the fifth linking portion 55 are disposed at the positions that form the parallelogram, to thereby configure a (third) parallelogram link mechanism. The (third) parallelogram link mechanism functions as reverse operation preventing means that prevents the (second) parallelogram link mechanism from operating reversely to be in a functional incompetence in the case where the endoscope 2 held by the holding portion 20 is moved in the up/down direction, to thereby cause the first link 11 to rotate around the first linking portion 51 (horizontal axis H1), and thereafter the first link 11 and the fifth link 15 are brought into the state where the first link and the fifth link coincide with the vertical axis V (vertical state).

In the present embodiment, in order to bring the first link 11 and the fifth link 15 into the vertical state where the first link and the fifth link coincide with the vertical axis V in the (second) parallelogram link mechanism, the first, third, fourth, and eleventh linking portions (51, 53, 54, and 61) have to be aligned on a straight line. In order to achieve the state, it is required to make "a sum of a distance [L1A] between the first and eleventh linking portions (51, 61) and a distance [L2A] between the eleventh and the fourth linking portions (61, 54)" completely coincide with "a sum of a distance [L1B] between the third and fourth linking portions (53, 54) and a distance [L2B] between the first and third linking portions (51, 53)". In view of the member machining accuracy, however, the complete coincidence is difficult to achieve. Therefore, in view of the variance in component tolerances, for example, the fourth linking portion 54 is supposed to be configured by providing a margin for allowing the variance in the tolerances in the (second) parallelogram link mechanism. In such a configuration, there is a case where the (second) parallelogram link mechanism operates reversely to be in a functional incompetence before and after the vertical state where the first link 11 and the fifth link 15 coincide with the vertical axis V.

In view of such a circumstance, in the endoscope holding apparatus 1 according to the present embodiment, the first link 11 and the sixth link 16 are provided with the first protruding portion 11d and the second protruding portion 16n, respectively, the respective protrusion portions are provided with the fifth and sixth linking portions (55, 56), and the fifth and sixth linking portions (55, 56) are linked to each other with the seventh link 17, to configure the (third) parallelogram link mechanism.

Note that, in this case, at the fourth linking portion 54 provided at the one arm portion 16m of the sixth link 16, an elongated hole or slit having a longitudinal axis extending in the direction along the extended direction of the link arm (one arm portion 16m) is formed as a fitting hole to which a linking shaft is fitted, though not shown. Therefore, the rotation shaft of the fourth linking portion 54 is fitted slidably in the elongated hole or slit. Providing such an elongated hole (slit) tolerates the difference between the distance [L1A] between the first and eleventh linking portions (51, 61) and the distance [L1B] between the third and fourth linking portions (53, 54).

Note that, as shown in FIG. 1, the support arm 8 is extended on the extended line of the fourth link 14 in the parallelogram link mechanism 7 in the present embodiment as described above. The proximal end of the support arm 8 is linked to the distal end of the fourth link 14 at the proximal end linking portion 43. At the distal end of the support arm 8, the holding portion 20 having a three-direction degree of freedom, for example, is linked. The holding portion 20 holds the endoscope 2.

Note that, as a specific configuration of the holding portion 20, an existing configuration formed by a ball and a holding part that holds a ball may be applied, for example. Therefore, illustration and description of the detailed configuration of the holding portion will be omitted.

In addition, it is preferable that the axis line H2 (see FIG. 1), which is along the support arm 8 arranged so as to extend on the extended line of the fourth link 14, is disposed so as to be substantially orthogonal to the eighth linking portion 58, the ninth linking portion 59, the first linking portion 51, and the second linking portion 52, which serve as rotation shafts in the parallelogram link mechanism 7. Such a configuration enables the center of gravity of the whole endoscope holding apparatus 1 to be easily put on the vertical axis V.

The two counterweights 41, 42 are hanged by the fifth link 15 and the second weight holding link 21, respectively, in the vertical direction on the side which is opposite to the side on which the endoscope 2 is held, across the first linking portion 51 as the rotation center of the parallelogram link mechanism 7. The counterweights 41, 42 are provided to cancel the rotational moment generated with the horizontal axis H1 as the center. Therefore, the endoscope 2 held by the holding portion 20 can be maintained at a desired arbitrary position.

The endoscope holding apparatus 1 thus configured according to the present embodiment is used, with the endoscope 2 as a medical instrument attached to the holding portion 20. In the state where the endoscope 2 as the medical instrument is attached to the holding portion 20, the endoscope 2 is moved in the horizontal direction by the support column 9 being rotated around the vertical axis V.

In addition, the endoscope 2 is moved in the up/down direction by the parallelogram link mechanism 7 (first to fourth links 11, 12, 13, and 14) rotating around the horizontal axis H1 with respect to the support column 9 at the first linking portion 51, and in accordance with the rotation, the link members (11, 12, 13, and 14) rotating around the rotation shafts (51, 52, 58, 58), respectively.

At this time, the (first) parallelogram link mechanism functions as the counterweight inclination restricting means, to restrict the inclination of the second counterweight 42 and constantly maintain the state where the second counterweight 42 is hanged in the vertical direction. In addition, the (second) parallelogram link mechanism functions as the counterweight inclination restricting means, to restrict the inclination of the first counterweight 41 and constantly maintain the state where the first counterweight 41 is hanged in the vertical direction. Furthermore, the (third) parallelogram link mechanism functions as the reverse operation preventing means, to prevent the (second) parallelogram link mechanism from operating reversely to be in the functional incompetence.

With such working, the user moves the medical instrument (endoscope 2) held by the holding portion 20 in the horizontal direction and the up/down direction, to arrange the medical instrument at a desired arbitrary position.

As described above, according to the first embodiment, the fifth link 15 and the second weight holding link 21 that respectively hold the two counterweights 41, 42 are disposed hanged in the vertical direction, which is capable of suppressing the protruding amounts of the counterweights.

In addition, the other end (lower end side) of the fifth link 15 hanged in the vertical direction is linked by the one arm portion 16m of the sixth link 16 as the parallel link which is paired up with the short arm portion 11b of the first link 11, which prevents the counterweight in the hanged state from swinging. As a result, stable operation can be ensured.

Similarly, the other end (lower end side) of the second weight holding link 21 hanged in the vertical direction is linked by the ninth link 19 as the parallel link which is paired up with the second link 12, which prevents the counterweight in the hanged state from swinging. As a result, stable operation can be ensured.

The links 15, 21 themselves, which respectively hold the counterweights, may be configured by using a material having a weight, to enable the links themselves to function as the counterweights. The counterweights are thus formed in an elongated shape, for example, to thereby be capable of further reducing the protruding region of the counterweights.

The first linking portion 51, the third linking portion 53, the tenth linking portion 60, and the second linking portion 52 are disposed at the positions that form the parallelogram, to thereby configure the (first) parallelogram link mechanism. With such a configuration, the (first) parallelogram link mechanism functions as the counterweight inclination restricting means, to restrict the inclination of the second counterweight 42 to constantly maintain the state where the second counterweight 42 is hanged in the vertical direction.

Similarly, the first linking portion 51, the third linking portion 53, the fourth linking portion 54, and the eleventh linking portion 61 are disposed at the positions that form the parallelogram, to thereby configure the (second) parallelogram link mechanism. With such a configuration, the (second) parallelogram link mechanism functions as the counterweight inclination restricting means, to restrict the inclination of the first counterweight 41 and constantly maintain the state where the first counterweight 41 is hanged in the vertical direction.

Furthermore, the first linking portion 51, the third linking portion 53, the sixth linking portion 56, and the fifth linking portion 55 are disposed at the positions that form the parallelogram, to thereby configure the (third) parallelogram link mechanism. With such a configuration, the (third) parallelogram link mechanism functions as reverse operation preventing means, to thereby be capable of preventing the (second) parallelogram link mechanism from operating reversely to be in the functional incompetence in the case where the endoscope 2 held by the holding portion 20 is moved in the up/down direction, to thereby cause the first link 11 to rotate around the first linking portion 51 (horizontal axis H1), and thereafter the first link 11 and the fifth link 15 are brought into the state where the first link and the fifth link coincide with the vertical axis V (vertical state).

Second Embodiment

Figure 5:
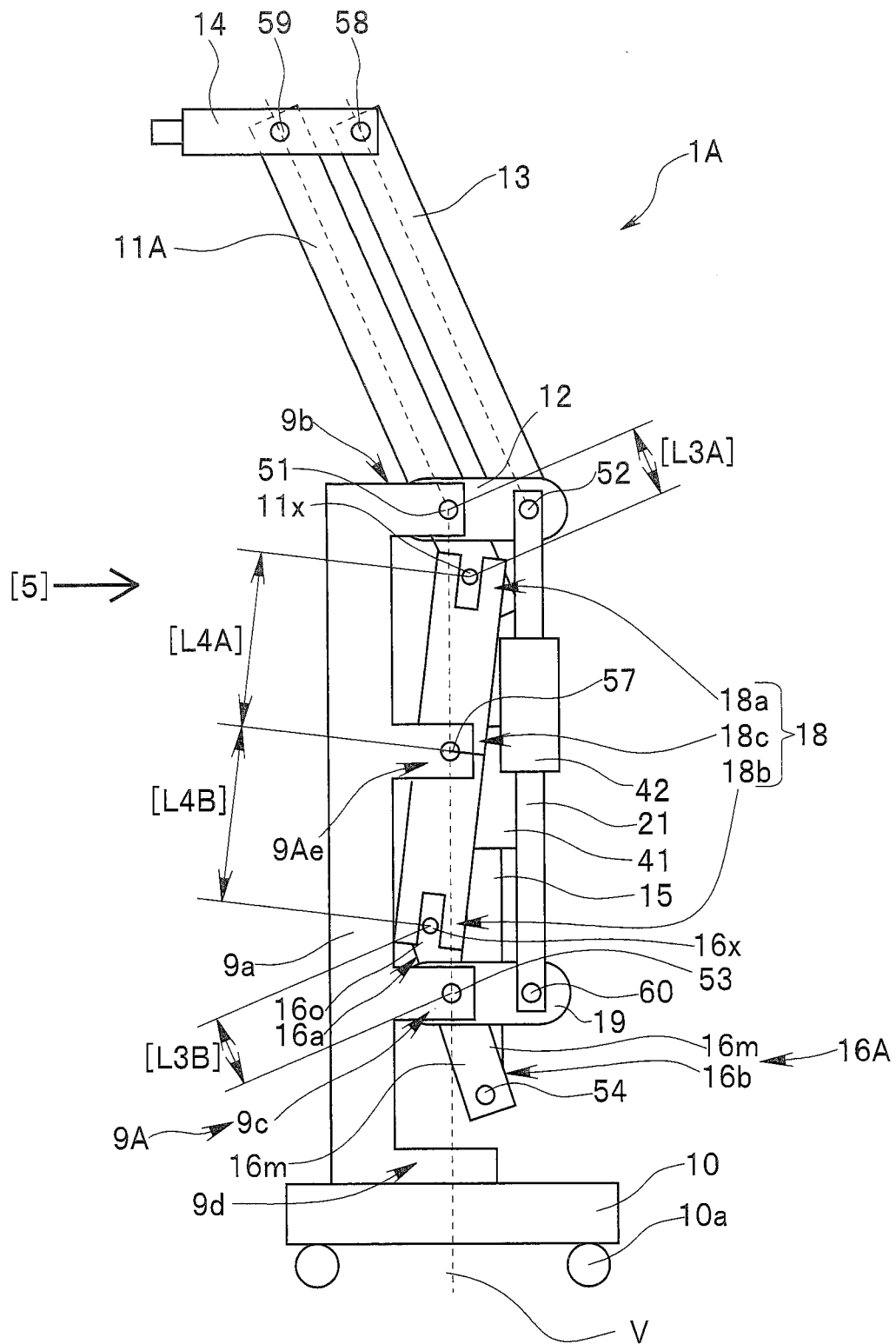
FIG. 5 is a schematic configuration diagram of an endoscope holding apparatus according to a second embodiment of the present invention.
Figure 6:
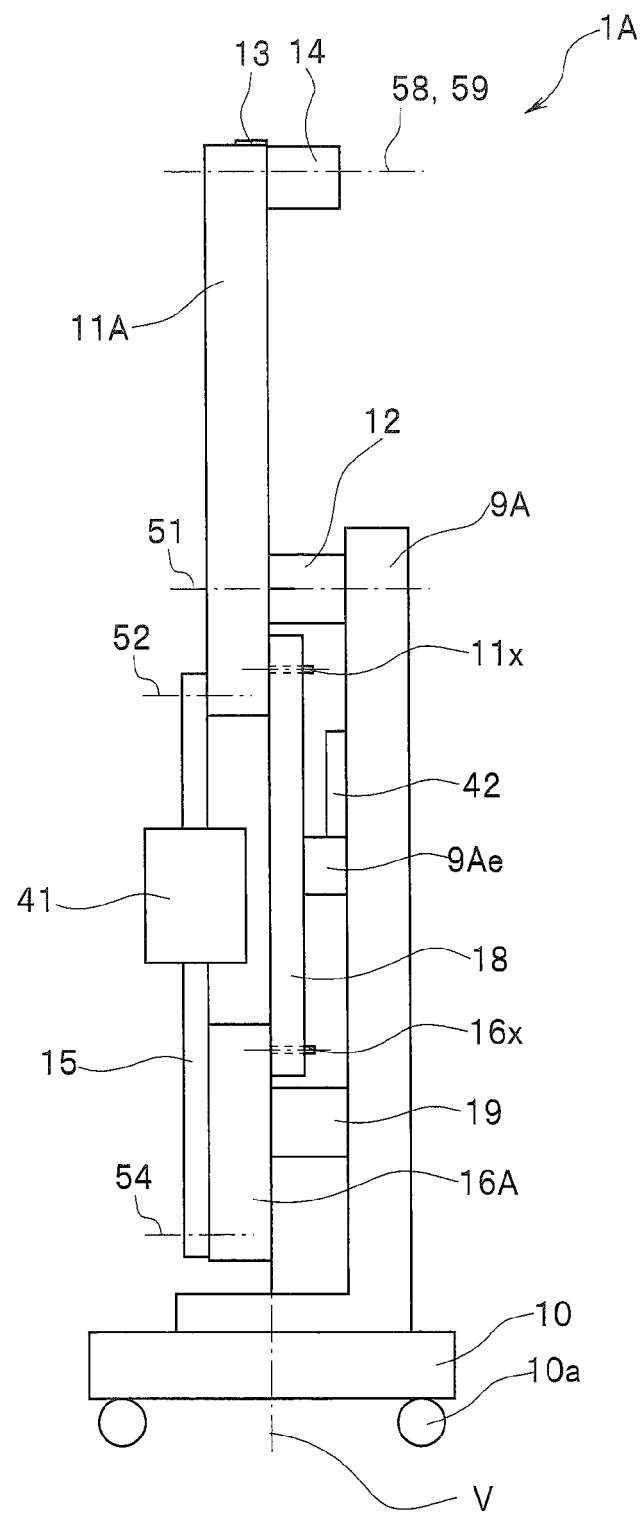
FIG. 6 is a main configuration diagram of the endoscope holding apparatus viewed from the direction of the arrow sign [5] in FIG. 5.

Next, description will be made on an endoscope holding apparatus according to the second embodiment of the present invention with reference to FIGS. 5 and 6. FIG. 5 is a schematic configuration diagram of the endoscope holding apparatus according to the second embodiment of the present invention. FIG. 6 is a main configuration diagram of the endoscope holding apparatus viewed from the direction of the arrow sign [5] in FIG. 5. Note that also in FIGS. 5 and 6, illustrations of the support arm portion that holds the endoscope or the like and the medical instrument such as the endoscope held by the support arm portion are omitted, and only the main configuration part of the endoscope holding apparatus according to the present embodiment is shown.

The basic configuration of the present embodiment is substantially the same as that in the above-described first embodiment. In the present embodiment, the shapes of the support column, first link, and sixth link among the constituent elements are slightly different from those in the first embodiment, and an eighth link is provided as a new constituent element. Therefore, the same constituent elements as those in the above-described first embodiment are attached with the same reference signs and descriptions thereof will be omitted in the description below, and only a different configuration will be detailed below.

An endoscope holding apparatus 1A according to the present embodiment is same as the one in the first embodiment in that a parallelogram link mechanism is supported at the base 10 placed on the floor of the clinical room, through the support column 9.

On the upper surface of the base 10, the support column 9A is vertically arranged so as to be rotatable with the vertical axis V as the rotation center. The support column 9A according to the present embodiment includes: the pole portion 9a; the first arm portion 9b; a second arm portion 9c that extends in the horizontal direction from a part which is in the middle of the pole portion 9a and closer to the lower end of the pole portion 9a; a third arm portion 9Ae that extends in the horizontal direction from a part which is in the middle of the pole portion 9a and which is a region between the first arm portion 9b and the second arm portion 9c; and the proximal end portion 9d. That is, the present embodiment is different in that the third arm portion 9Ae is newly provided and the second arm portion 9c is provided at the position which is closer to the lower end.

In the present embodiment, the first arm portion 9b is provided with the first linking portion 51, and the base portion 11a of the first link 11 and the one end of the second link 12 are rotatably linked to the first arm portion 9b at the first linking portion 51, similarly as in the first embodiment. In addition, similarly as in the first embodiment, the second arm portion 9c is provided with the third linking portion 53, and the base portion 16a of the sixth link 16 and the proximal end of the ninth link 19 are rotatably linked to the second arm portion 9c at the third linking portion 53.

The third arm portion 9Ae of the support column 9 according to the present embodiment is provided with the seventh linking portion 57, and the eighth link 18 to be described later is rotatably linked to the support column 9 at the seventh linking portion 57. Other configurations of the support column 9A are the same as those of the support column 9 in the above-described first embodiment.

The sixth link 16A includes the one arm portion 16m and a third protruding portion 16o, which are each extended from the base portion 16a. That is, the sixth link 16A is same as the sixth link 16 in the first embodiment in the configuration of the one arm portion 16m, but different in that the second protruding portion 16n of the sixth link 16 in the first embodiment is not provided. The present embodiment is different from the first embodiment in that the third protruding portion 16o is formed on the extended line of the one arm portion 16m at a position across the base portion 16a. The third protruding portion 16o is slidably and rotatably engaged with a second end 18b of the eighth link 18 to be described later.

The first link 11A is formed by including the short arm portion 11b and the long arm portion 11c, which are extended from the base portion 11a. The first link 11A according to the present embodiment is different from the first link 11 in the first embodiment in that the first protruding portion 11d is not provided. As described later, a first end 18a of the eighth link 18 is rotatably engaged with the first link 11A.

The eighth link 18 is an elongated link member and formed by including a center portion 18c in the longitudinal direction, the first end 18a positioned on one end with respect to the center portion 18c, and a second end 18b positioned on the opposite side of the first end 18a across the center portion 18c.

In addition, slit portions to which fitting pins to be described later are fitted are formed in the vicinity of the respective distal end portions of the first end 18a and the second end 18b of the eighth link 18, the slit portions being formed in the shape of a groove or cutout extending in the longitudinal direction.

In the slit portion located at the first end 18a of the eighth link 18, a fitting pin 11x provided in a protruded manner on the short arm portion 11b of the first link 11 is slidably fitted. With such a configuration, the first end 18a of the eighth link 18 is slidably and rotatably engaged with the short arm portion 11b of the first link 11.

In addition, in the slit portion located at the second end 18b of the eighth link 18, a fitting pin 16x provided in a protruded manner on the third protruding portion 16o of the sixth link 16 is slidably fitted. With such a configuration, the second end 18b of the eighth link 18 is slidably and rotatably engaged with the third protruding portion 16o of the sixth link 16.

The eighth link 18 thus configured has the center portion 18c rotatably and pivotally supported at the seventh linking portion 57 of the third arm portion 9Ae of the support column 9. In this case, the eighth link 18 is disposed so as to be inclined with respect to the fifth link 15 that holds the first counterweight 41.

Note that the parallelogram link mechanism 7 is configured by the first to fourth links 11A, 12, 13 and 14 in the present embodiment. In addition, similarly as in the first embodiment, the first linking portion 51, the third linking portion 53, the tenth linking portion 60, and the second linking portion 52 configure the (first) parallelogram link mechanism. Furthermore, in the present embodiment, a line connecting the first linking portion 51 and the fitting pin 16x, a line connecting the third linking portion 53 and the fitting pin 16x, a line connecting the first linking portion 51 and the fitting pin 11x, and a line connecting the third linking portion 53 and the fitting pin 11x form a parallelogram. In other words, the first linking portion 51, the third linking portion 53, the fitting pin 16x, and the fitting pin 11x are disposed at the positions that form the parallelogram, to configure a (fourth) parallelogram link mechanism. The (fourth) parallelogram link mechanism functions as reverse operation preventing means that prevents the (fourth) parallelogram link mechanism from operating reversely to be in a functional incompetence in the case where the endoscope (2) held by the holding portion (20) is moved in the up/down direction, to thereby cause the first link 11A to rotate around the first linking portion 51 (horizontal axis H1), and thereafter the first link 11A and the fifth link 15 are brought into the state where the first link and the fifth link coincide with the vertical axis V (vertical state).

In the present embodiment, a distance [L3A] between the first linking portion 51 and the fitting pin 11x is set to be equal to a distance [L3B] between the third linking portion 53 and the fitting pin 16x. In addition, a distance [L4A]

between the eleventh linking portion 57 and the fitting pin 11x is set to be equal to a distance [L4A] between the eleventh linking portion 57 and the fitting pin 16x. Other configurations are the same as those in the first embodiment.

As described above, according to the second embodiment, the eighth link 18 is provided, to thereby be capable of suppressing the reverse operation of the (fourth) parallelogram link mechanism. In this case, the fitting pin 11x of the short arm portion 11b of the first link 11 and the fitting pin 16x of the third protruding portion 16o of the sixth link 16 are respectively fitted in the slit portions provided respectively on the both ends (18a, 18b) of the eighth link 18, to thereby be capable of tolerating the difference between the distance [L3A] and the distance [L3B].

Note that the present invention is not limited to the above-described embodiments, and it is needless to say that various modifications and application can be performed in a range without departing from the gist of the invention. Furthermore, the embodiments include the inventions at various stages, and various kinds of inventions can be extracted by appropriately combining a plurality of disclosed constituent elements. For example, even if some constituent elements are deleted from all the constituent elements shown in the one embodiment, the configuration from which some constituent elements are deleted can be extracted as the invention if the problem to be solved by the invention can be solved and the effects of the invention can be obtained. Furthermore, constituent elements in different embodiments can be appropriately combined. The present invention is not limited to particular embodiments thereof except insofar as the same is limited by appended claims.

The present invention can be applied not only to an endoscope holding apparatus in medical fields but also to an endoscope holding apparatus in industrial fields.

What is claimed is:

1. An endoscope holding apparatus comprising:
    a base section;
    a support column connected to the base section;
    a first link including a short arm portion, a long arm portion, and a first protruding portion that are extended from a base portion, the base portion being rotatably linked to the support column at a first linking portion;
    a second link rotatably linked to the support column and the first link at the first linking portion;
    a third link rotatably linked to the second link at a second linking portion provided at the second link;
    a fourth link rotatably linked to the first link and the third link, and configured to maintain the first link and the third link in parallel with each other, the fourth link being maintained in parallel with the second link and configured to be capable holding an endoscope at an end portion of the fourth link;
    a fifth link including a first end and a second end, the first end being rotatably linked to an end portion of the short arm portion of the first link, the fifth link including a first counterweight which is hanged in a vertical direction at a middle portion between the first end and the second end;
    a second counterweight rotatably linked to the second linking portion and hanged in the vertical direction;
    a sixth link including one arm portion and a second protruding portion that are extended from a base portion, the base portion being rotatably linked to the support column at a third linking portion, the one arm portion being rotatably linked to the second end of the fifth link at a fourth linking portion, the one arm portion being maintained in parallel with the first link; and
    a seventh link including a first end and a second end; the first end being rotatably linked at a fifth linking portion of the first protruding portion, the second end being rotatably linked at a sixth linking portion of the second protruding portion,
    wherein the first linking portion, the fifth linking portion, the sixth linking portion, and the third linking portion are disposed at positions that form a parallelogram.

2. The endoscope holding apparatus according to claim 1, further comprising
    an eighth link including a center portion in a longitudinal direction, a first end positioned on one end with respect to the center portion, and a second end positioned on an end opposite to the first end across the center portion,
    wherein the eighth link is configured such that the center portion is rotatably linked to the support column at a seventh linking portion,
    the first end is rotatably engaged with the first link,
    the second end is rotatably engaged with a third protruding portion formed by being extended from the base portion of the sixth link, and
    the eighth link is disposed so as to be inclined with respect to the fifth link.

* * * * *